United States Patent [19]

Hesselgren

[11] 3,964,164

[45] June 22, 1976

[54] METHOD OF APPLYING PREVENTIVE AND THERAPEUTIC AGENTS

[76] Inventor: Sven-Gunnar Hesselgren, Angsholmen, S-170 11 Drottningholm, Sweden

[22] Filed: Jan. 25, 1974

[21] Appl. No.: 436,737

[30] Foreign Application Priority Data

Feb. 5, 1973 Sweden............................ 73015448

[52] U.S. Cl............................................ 32/1; 32/17; 128/260; 424/16
[51] Int. Cl.² ...................... A61C 19/00; A61K 9/00
[58] Field of Search.................. 32/17, 19, 14 B, 15, 32/1; 424/52, 16; 128/136, 260

[56] References Cited
UNITED STATES PATENTS

| | | |
|---|---|---|
| 2,021,058 | 11/1935 | Harrison ............................. 32/17 X |
| 3,527,219 | 9/1970 | Greenberg ...................... 128/136 X |
| 3,536,069 | 10/1970 | Gores................................... 128/136 |
| 3,688,406 | 9/1972 | Porter et al...................... 128/260 X |
| 3,822,345 | 7/1974 | Murray ................................ 424/52 |
| 3,844,286 | 10/1974 | Cowen................................. 128/260 |

Primary Examiner—Louis G. Mancene
Assistant Examiner—Jack O. Lever
Attorney, Agent, or Firm—Murray, Schaffer

[57] ABSTRACT

The invention concerns a method and composition for local application of an active preventive and/or therapeutic agent in the oral cavity by means of a carrier into which the active agent is incorporated. The carrier is an initially mouldable mass which after application is converted into a tough or viscous, elastic consistency.

5 Claims, No Drawings 3,964,164

METHOD OF APPLYING PREVENTIVE AND THERAPEUTIC AGENTS

BACKGROUND OF THE INVENTION

The present invention relates to a method for local application of an active preventive and/or therapeutic agent on teeth and the tissues surrounding the teeth in the oral cavity, and a composition for use with this method.

By experimental investigations and practical application it has been proved that certain chemical substances when applied locally are effective agents in preventing the occurrrence or reducing the spreading of pathological alterations in the teeth and surrounding tissues.

An example of such a substance is fluorine which is used to a great extent in odontology, for instance for painting the teeth with the object of preventing caries. Another example is chlorohexidine which is used locally for both therapeutic and preventive purposes.

For fluorine treatment, for example, limited sections of the dental arch, usually a quadrant corresponding to 8 – 5 teeth in the upper or lower jaw, are painted or coated using pieces of cotton or gauze which have been dipped in a fluorine solution of suitable concentration, after which the fluorine solution applied in this way is permitted to influence the tooth tissue for a certain period of time. During this time of exposure it is necessary to prevent mouth saliva and lips, cheeks and tongue from coming into contact with the area which has been treated. For this purpose special drying arrangements are used such as the mounting of saliva suction means, the application of wadding dryer or other steps such as the application of cofferdam. These steps are extremely uncomfortable for the patient and are used to prevent saliva from reaching the tooth surfaces since by diluting or rinsing off the active substance the saliva reduces or destroys the intended effect of the treatment. This effort to avoid saliva coming into contact with the tooth surfaces thus also involves keeping the patient under constant observation during the treatment. Another drawback with the described method of application is that there is also a risk of the patient swallowing the fluorine solution or of the fluorine solution coming into contact with other parts of the mouth than those parts intended for treatment. Only after treatment of one section has been completed can preparations for and treatment of the next section be undertaken until all teeth have been treated with the fluorine solution.

It will be understood from the above that the method of application described above which has been in general use hitherto is both timeconsuming and laborious. There is also a factor of uncertainty as to the result of the treatment, particularly in the case of patients who are generally difficult to treat or children who are very lively.

SUMMARY OF THE INVENTION

It has now been found that the drawbacks mentioned above can be satisfactorily eliminated by applying the active agent in accordance with the present invention. The novel method is substantially characterised in that the active agent is applied with the help of a carrier in which the agent has been incorporated, said carrier when it is to be applied being made into or consisting of a mouldable mass or material which is compatible with the active agent, said mass is converted into a tough or viscous, elastic consistency after application, as a result of solidification accelerators included in the mass or added when the mass is prepared. Said agent comprises one or more substances having preventive and/or therapeutic actions.

Although the invention can be utilized for a series of different applications, it will be described specifically with respect to odontological use.

The initially mouldable carrier may preferably consist of any type of plastic or elastic impression mass or material for dental use, such as impression wax and wax compositions, reversible and irreversible hydrocolloidal impression masses, rubber impression masses and the like. The active agent can be mixed into masses of this type in a manufacturing stage. Dental hydrocolloidal impression masses are based on gelatine or agar, usually with calcium sulphate as reactor. Various salts may be added to control the time of solidification. Rubber pastes are available in two types of dental impression material. The basis of one type is polysulphide and for the other silicon. These elastomers require an activator to be mixed in immediately prior to use.

An essential property of the impression mass or other mass used as carrier is that it shall be plastic prior to and in connection with application on the teeth and shall thereafter be converted into a tough or viscous, elastic consistency.

PREFERRED EMBODIMENT OF THE INVENTION

The following components are mixed in the weight proportions stated in order to produce a portion for application on one row of teeth in the upper or lower jaw:

| | |
|---|---|
| Potassium alginate | 12 percent by weight |
| Kieselguhr | 72 percent by weight |
| Calcium sulphate (dihydrate) | 12 percent by weight |
| Sodium fluoride | 4 percent by weight |

The exact proportions of the substances used vary according to the type of raw material. If 15 g of the powder are mixed with 50 ml water, the compound or mass will generally solidify within 6 to 8 minutes at room temperature. The kieselguhr or fuller's earth acts as filler, gives a smooth surface and prevents the mass from adhering to the surface on which it is placed when it solidifies. In order to extend the time of solidification trisodium phosphate, for example, may be added in a suitable amount. Calcium sulphate is used to give body to the composition upon solidification (reactor).

After mixing with a suitable quantity of water the plastic mass is transferred to a mould consisting of a so-called impression spoon for dental use, which is designed to enclose all the teeth in the upper or lower jaw. While the mass containing fluorine is still in plastic state, the spoon with its contents is placed in the patient's mouth, after which the mass is brought to surround all exposed surfaces of the teeth by slight pressure on the spoon. In this way even the surfaces which are difficult in access and therefore expecially prone to caries, such as the approximate or adjacent surfaces, will come into contact with the active substance in the mass in a simple but efficient manner. Due to its viscous consistency portions of the mass are prevented from running down into the throat and the risk of swallowing or inhaling undesirable substances has thus been eliminated. The invention also enables efficient control and limitation of the effect of the active substance to those sections and surfaces which are intended to be treated.

Since the mass solidifies rapidly as a result of the increased temperature in the mouth, the spoon need only be held in position initially for a short while by the operator. The spoon with its contents stays in position on its own for the rest of the exposure time, without assistance from the dental personnel.

From the moment when the spoon containing the mass is applied, active fluorine is continuously distributed to all exposed surfaces. This has been shown during laboratory tests in which measurements were taken using, for example, fluorine electrodes which had been immersed in the mass. By adjusting the concentration and type of active agent, the desired therepy can be achieved. At the end of the exposure time the elastic mass shaped to an impression is removed, it having become firmly secured in one piece in the spoon provided with retention means, without leaving undesired rests of mass in the mouth and without damaging the teeth and soft tissues.

The method according to the invention is satisfactory from the hygienic point of view since portions adapted for individual need of treatment can be prepared and then thrown away after completion of the treatment, together with the spoon if this is of the disposable type. Alternatively the impression may be stored for repeated treatment of the same patient on a later occasion, by packing it in a moisture-retaining wrapper, such as a plastic bag. Electrometric measurements have shown that even when the same impression is used for repeated treatment the active agent is distributed to the contact surfaces. This makes the method even more time and labour saving, as well as economically advantageous. The use of disposable impression spoons facilitates the procedure.

When using an impression mass based on a powder composition and an addition of water, individual packs of the powder composition may be a further advantage. The decomposition which often occurs during storage in bulk as a result of the different specific weight of the individual components has no detrimental effect when using individual packets where the total content of the packet is mixed with water. This ensures exact dosing of the active agent.

Other suitable fluorine compounds which can be applied in this way and which are considered to be especially effective in preventing caries are, for example, stannous fluoride, potassium fluoride, monofluorine phosphate, etc.

The quantity of active agent in the carrier may be varied within wide limits and is dependent on a number of factors, such as the treatment intended, the type of active substance, the time of exposure of the active substance, etc., and no general limits of quantity can therefore be given. When applying fluorine on tooth tissue in the form of NaF, for example, the quantity may be 4 per cent or equivalent to the degree of saturation, down to extremely small therapeutic quantities (0.001 per cent).

The following test was effected to ascertain the distribution of growth-inhibiting agents from alginate composition mixed with inhibitor to surrounding teeth when taking dental impressions in the mouth.

A number of portions of powder of an alginate composition were measured out. 0.2 per cent by weight of chlorohexidine diacetate in powder form was added to each portion together with a specific quantity of water. Each portion mixture was mixed for 1 minute using a spatula so that a homogenous, thick, pastelike mass was obtained.

The mass was then transferred with the spatula to a perforated impression spoon and placed in the mouth so that the mass was pressed up over the teeth in the upper or lower jaw. The viscous consistency of the mass caused the spoon with its contents to remain in this position without having to be secured in any other way. After 3 minutes the spoon was removed together with the mass which had then solidified to form an elastic, rubbery consistency. The mass was firmly anchored to the spoon by the retention in the perforations in the spoon.

Liquid bacteriological substrate for cultivating oral bacteria was then poured into the saliva-covered tooth impression. The impression was placed in a thermostat at 37° C. A daily reading was performed to ascertain whether any bacteria growth had occurred. Any evaporation of substrate was compensated by the addition of fresh cultivation liquid so that the impression was filled with cultivation medium during the entire incubation period. The cultivation tests were continued for 10 days. Control tests were performed in a similar manner using powder alginate composition without the addition of growth inhibitor (chlorohexidine diacetate).

No growth of micro-organisms could be found in the impressions where alginate composition with chlorohexidine diacetate had been used. There was profuse growth of oral micro-organisms even after twentyfour hours cultivation in all the tests performed without using inhibitor. This growth had arisen from saliva remaining in the impression.

The above tests show that an impression mass with the addition of growth-inhibiting substances inactivates oral bacteria coming into contact with the mass. Thus, the method according to the present invention can be advantageously utilized for local application of a bactericidal agent.

The invention is not limited to the examples described above for applying fluorine and chlorohexidine but can be used more widely in the treatment of teeth and their surrounding tissue, using other preventive and therapeutic substances incorporated in a mouldable mass, preferably an impression mass for dental use.

What I claim is:

1. A method for local application of a therapeutic agent on the teeth and the tissues surrounding the teeth, comprising the steps of admixing an active therapeutic agent with a carrier formed of an inert solid composition capable of being converted to a highly viscous shape retaining elastic consistency, forming said admixture into a moldable mass, introducing said mass into the mouth and applying it onto the teeth and the tissues surrounding the same, allowing said mass to solidify in situ about said teeth and surrounding tissues and leaving said solidified mass in contact with the teech and said surrounding tissues for a time period sufficient for migration of said active agent from said carrier onto the teeth and said surrounding tissues to effect therapeutic treatment thereof and then removing the solidified mass from the mouth.

2. The method according to claim 1, wherein said carrier is a dental impression mass selected from the group consisting of wax impression masses, hydrocolloidal impression masses and rubber impression masses.

3. The method according to claim 1, including the step of adding to said carrier an agent adapted to control the rate of hardening of said mass.

4. The method according to claim 1, comprising the step of placing the admixture of the carrier and the active agent on a mold conforming to the configuration of said teeth, bringing said mass into intimate contact with all the surfaces of the teeth and tissues to be treated and thereafter keeping the mold in place for a period of time sufficient for transition of the active agent onto said teeth and tissue surfaces.

5. The method according to claim 1, comprising the step of using as the active agent fluorine compounds releasing fluorine ions when the compound is brought in contact with tooth and tooth surrounding tissues.

* * * * *